US007438681B2

(12) United States Patent
Kobashikawa et al.

(10) Patent No.: US 7,438,681 B2
(45) Date of Patent: Oct. 21, 2008

(54) ELECTRONIC VARIABLE STROKE DEVICE AND SYSTEM FOR REMOTE CONTROL AND INTERACTIVE PLAY

(76) Inventors: Alvin Y. Kobashikawa, 99-421 Poaha Pl., Aiea, HI (US) 96701; Rita E. Iwakawa, 311 Ohua Ave., #604D, Honolulu, HI (US) 96815

( * ) Notice: Subject to any disclaimer, the term of this patent is extended or adjusted under 35 U.S.C. 154(b) by 858 days.

(21) Appl. No.: 10/687,729

(22) Filed: Oct. 16, 2003

(65) Prior Publication Data

US 2004/0082831 A1 Apr. 29, 2004

Related U.S. Application Data

(60) Provisional application No. 60/419,554, filed on Oct. 17, 2002.

(51) Int. Cl.
*A61F 5/00* (2006.01)

(52) U.S. Cl. ........................................ 600/38

(58) Field of Classification Search ............ 600/38–41, 600/595; 128/897, 898, 904, 905
See application file for complete search history.

(56) References Cited

U.S. PATENT DOCUMENTS

| | | | | |
|---|---|---|---|---|
| 1,516,717 | A | 11/1924 | Coleman | |
| 3,216,225 | A * | 11/1965 | Artigas | 68/23.3 |
| 3,873,985 | A * | 3/1975 | Altmayer | 343/714 |
| 5,676,637 | A | 10/1997 | Lee | |
| 5,984,880 | A | 11/1999 | Lander | |
| 6,028,531 | A | 2/2000 | Wanderlich | |
| 6,190,307 | B1 | 2/2001 | Tsai | |
| 6,251,066 | B1 | 6/2001 | Pack | |
| 6,368,268 | B1 | 4/2002 | Sandvick | |
| 6,422,993 | B1 | 7/2002 | Hudson | |
| 6,592,516 | B2 * | 7/2003 | Lee | 600/38 |
| 6,632,185 | B2 * | 10/2003 | Chen | 601/101 |
| 6,695,770 | B1 * | 2/2004 | Choy et al. | 600/38 |
| 7,510,031 | | 2/2004 | Wantz | |
| 7,104,950 | B2 * | 9/2006 | Levy | 600/38 |
| 2003/0036678 | A1 * | 2/2003 | Abbassi | 600/38 |

OTHER PUBLICATIONS

Sinulator Web Site, "Cam Networks and Performers", "Product Information", 2003, published at www.sinulate.com.

(Continued)

*Primary Examiner*—Samuel G Gilbert
(74) *Attorney, Agent, or Firm*—Leighton K. Chong

(57) ABSTRACT

An electronic reciprocation device has a base containing a motor-driven screw shaft, an upper body having the screw shaft extending longitudinally therein, and a traveler engaged with the screw shaft to drive the upper body in positioning and reciprocating motion. A remote control unit can be used for comfortable operation of the device. A network connection unit is provided to connect the user's device to an external service website on the Internet or other networks. The user's device may be adapted as a male or female sex toy, and can exchange control signals on the Internet with one or more other users operating complementary sex toys. The Internet service can host interactive sessions with other users, groups of users, and even non-participating spectators. It preferably has a 3-tier structure of an administrator tier, hosted services tier, and affiliated play host tier for expansive offerings of interactive services to its users.

29 Claims, 8 Drawing Sheets

OTHER PUBLICATIONS

Hassex, Inc., "Method and Device for Interactive Virtual Control of Sexual Aids Using Digital Computer Networks", May 2003, published at hassexinc.com.

"The Love Machine", from Future Sex Magazine, San Francisco, CA, 1992.

Monaghan, C., "Plug Me In, Turn Me On", LA Weekly, Cyber Feature, Jun. 11-17, 1999.

Safe Sex Plus, "SSP Adapter", product decription, 1999, printed from www.safesexplus.com/pages/SSP_Converter.htm.

Safe Sex Plus, "The Internet Never Feft So Good", 1999, printed from www.safesexplus.com.

* cited by examiner

ELECTRONIC VARIABLE STROKE DEVICE AND SYSTEM FOR REMOTE CONTROL AND INTERACTIVE PLAY

This U.S. Patent Application claims the priority filing date of U.S. Provisional Application No. 60/419,554 filed on Oct. 17, 2002, by the same inventors, entitled "Electronic Variable Stroke Device".

TECHNICAL FIELD

This invention relates to an improved device for sexual or massage stimulation, and particularly one which is electronically controlled for variable stroke operation and which may be used advantageously in a system for remote control and interactive play on the Internet.

BACKGROUND OF INVENTION

There has previously been provided a great variety of sexual stimulation devices, sexual aids and other adult novelty toys. The well-known female vibrator has had the same basic configuration for a long time, namely, a fixed elongated outer shell to which vibrations are imparted by a battery-powered motor contained in the interior of the device. The vibrator can be used for sexual stimulation as well as massage to the muscles and tissues of the body for the benefits of relaxation and pleasure, as well as to enhance the physiological or psychological well being of people with certain limitations or disabilities. Other claimed benefits include the prevention of transmitted diseases, and maintaining marital harmony.

However, the prior devices have limited variability in motion. They typically have a fixed outer shape that only vibrates and cannot provide longitudinal stroke motion. Some prior devices have provided limited longitudinal reciprocation but not a longitudinal stroke motion. For example, in U.S. Pat. No. 751,031 to Wantz, a massage vibrator has a rotary shaft and cam follower arrangement for producing pounding (longitudinal) movements or rubbing (rotary) movements of a massager end. U.S. Pat. No. 1,516,717 to Coleman discloses a massage vibrator with a crown cam connector in the output shaft to provide longitudinal vibrations. U.S. Pat. No. 6,190,307 to Tsai discloses an eccentric vibratory device which produces transverse oscillation constrained to the diameter of the device, but also does not provide longitudinal stroke motion. U.S. Pat. No. 4,722,327 to Harvey and U.S. Pat. No. 5,076,261 to Black disclose female sex therapeutic devices that produce horizontal stroke motions, however, these are obtained by cumbersome eccentric disk and yoke follower arrangements contained in a bulky motor-drive housing. Thus, the prior stimulation or massage devices have not provided horizontal stroke motion which is obtained with a compact form factor and which can provide wide variability in stroke motion.

The prior devices also have limited user controls and fixed or limited variability of use. Many are designed as larger electromechanical devices that are cumbersome to use and operate and are further constrained by attached wires. Smaller hand-held devices have used electronic controls to reduce the size of the device, however, they are not designed to handle substantial reaction forces. Physical reaction forces must be absorbed by the support provided by the user as well as the device itself, thereby limiting the effectiveness of the device's output motions.

Recent proposals have attempted to link the control of a sex toy device to a computer connected to a network to provide stimulation to a person remotely. For example, U.S. Pat. No. 6,368,268 to Sandvick discloses a system for interactive virtual control of sexual aids on a network in which one or more users are connected by their computers to a web site and can enter control inputs on an input device connected to their computers which are transmitted as control signals to a remote device of another user while transmitting a video image to be seen on the computer display of the remote user. U.S. Pat. No. 5,984,880 to Lander similarly discloses an interactive remote control system in which input on a haptic or force-feedback input device connected to one user's computer results in control signals being transmitted to a remote stimulation device connected to another user's computer. However, such systems require the user(s) to enter control input and/or be imaged on a video camera while seated or positioned near their computer and display, which may not provide a sufficiently convenient or relaxing environment for the intended purpose of sending or receiving sexual stimulation.

SUMMARY OF INVENTION

It is therefore a principal object of the present invention to provide an electronically-controlled, variable stroke reciprocating device that is multi-functional and compact, yet has extensive variability of stroke motions and operating modes, and is also capable of remote control away from a user's computer desk, as well as interactive virtual control by a network connection, while maintaining a convenient and relaxing environment for sending or receiving stimulation. It is a particular object of the invention to provide such an electronic variable stroke device which can be used for sexual stimulation as well as massage to the muscles and tissues of the body for relaxation and pleasure, as well as physiological or psychological well being.

In accordance with the present invention, an electronic variable stroke device comprises a base portion containing a motor and power source for rotating a screw shaft alternately in opposite rotational directions, an upper portion extending longitudinally from the base portion, wherein the rotary-driven screw shaft has a length extending longitudinally into the upper portion and is provided with screw threading thereon, and a screw-thread traveler or follower engaged with the screw shaft threading in order to drive a member constituting a part of the upper body in reciprocating longitudinal motion.

In a preferred embodiment of the invention, the electronic variable stroke device is provided with electronic controls which control rotation of the screw shaft to vary the length, extent, speed, and frequency of the upper body member's reciprocating longitudinal motion. The electronic controls can include stored motion programs for operating the device in different modes of reciprocating longitudinal motions. The configuration of the motor and power source positioned in the base portion in-line with the upper body, screw shaft and follower provides a compact design and generates low-impact reaction forces, as well as allows the device to be comfortably manipulated or positioned by a user.

The electronic variable stroke device can have the upper body together with an annulus may form a surrounding bulge similar in shape to the head of a penis for use as a female sex toy. A male sex toy version can employ the screw thread and follower arrangement for longitudinally stroking a male penis member with variable pressure elements. The device may also be adapted for use in simulating hydraulic or powered motions in other types of toys. The remote controller unit may also be used as a remote motion controller for other products in the radio-controlled hobby industry, or as a game controller in the game systems industry.

The preferred embodiment can also be operated with a hand-held remote controller unit which can operate the electronic variable stroke device by wireless (or wired if desired) transmission of control signals. The remote controller unit can also be used to store various motion programs for operating the electronic variable stroke device in various modes. A control circuit may be provided on an IC board in the base portion of the device and/or in the remote controller unit having an EPROM in which different motion programs are stored and selected according to user preference. The remote controller unit can also include a link by wireless (or wired if desired) transmission of control signals from and/or to the user's computer to download and/or upload device control signals and/or complete motion programs. The use of the hand-held remote controller unit allows the user to variably and selectively control the operation of the electronic variable stroke device, while maintaining a convenient and relaxing environment for sending or receiving stimulation.

The electronic variable stroke device of the present invention enables a user to have stimulation applied by virtual or remote control over the Internet or other networks. A network connection unit is provided as a multi-function platform from which transmission of signals between devices and the control of associated TV display, audio, and camera devices are directed. The user device or devices can receive control signals or downloaded motion programs through an Internet connection to a web site or to another remote user who has been granted remote access to the first user's session. This would enable two or more users in respective remote locations to engage in remote interactive stimulation via Internet for relaxation and pleasure at the user's convenience, for physiological or psychological well being of persons with physical limitations or disabilities, avoidance of unwanted dating, prevention of transmitted diseases, maintaining marital harmony for couples apart, etc.

Other associated devices such as a video camera, microphone, headphones, and audio/visual components may be used with the electronic variable stroke device of the present invention. Other stimulation devices such as vibrators, heating elements, and expansion devices may be used in conjunction with the electronic variable stroke device, and their corresponding functions can also be included in the controls of the remote controller unit and the device control to enhance the desired effects.

The electronic variable stroke device may also be adapted to power reciprocation movement to supplant the common "hydraulic arm" in toys, or as a motion feedback device, or as a servo control mechanism. The remote controller unit and interactive virtual control system via Internet may also be adapted to other interactive or remote control environments, such as interactive learning systems for children and adults, interactive gaming, interactive adult toys, interactive home care, health, and physical therapy, and interactive systems for the home building, maintenance, or security industries. Other applications for the Internet-based system for multi-user interaction include remote game-playing and virtual videoconferencing.

Other objects, features, and advantages of the present invention will be explained in the following detailed description of the invention having reference to the appended drawings.

DETAILED DESCRIPTION OF INVENTION

Female Toy Device

Figure 1:
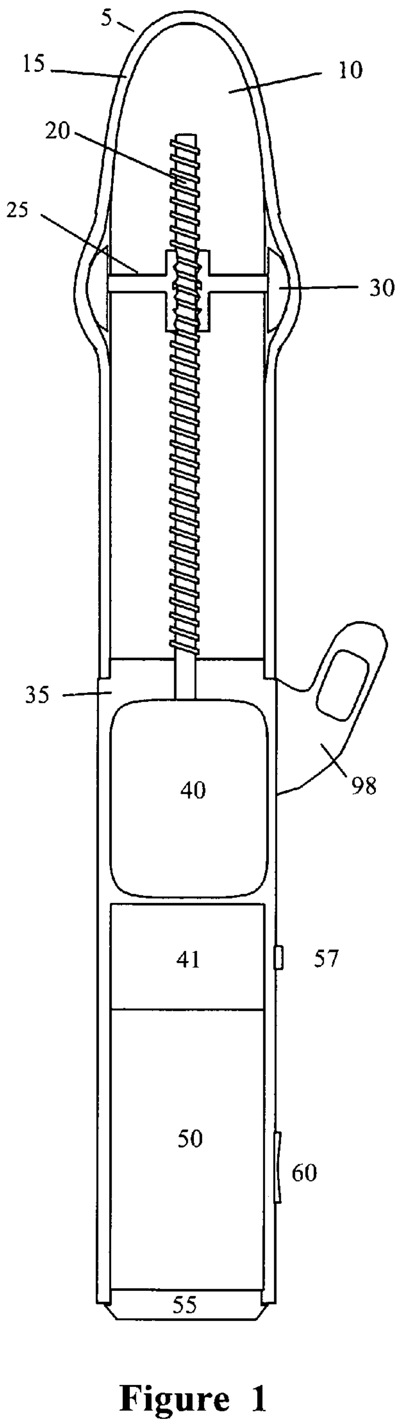
FIG. 1 shows a cross-sectional view of an electronic variable stroke device adapted as a female toy device in accordance with the present invention.

Referring to FIG. 1, there is shown a preferred embodiment of an electronic variable stroke device adapted as a female toy device 5 (also referred to shorthand as "FT") constructed and operated in accordance with the principles of the present invention. The main components of the electronic variable stroke mechanism consist of a base portion 35, an upper body portion 10, a rotary screw shaft 20, a traveler or follower 25 engaged with the threads of the screw shaft 20, an electric motor 40 located in the base portion 35 for driving the screw shaft in alternate rotational directions, and an electronic control circuit 41.

The screw shaft 20 may be made of metal, hard plastic, or some other suitable material. In some variations of the device having a slight curvature to simulate the shape of a penis, it may be suitable that the screw shaft be made of softer material to accommodate the curvature of the embodiment. The screw pitch will be determined by the amount of torque produced by the motor and the desired reciprocating speed. Traveler 25 can be constructed of metal, hard plastic, or other suitable material that is compatible with the screw to minimize wear characteristics such as friction and binding.

The upper body 10 is constructed from an appropriate material such as plastic for rigidity as well as flexibility. It may be desirable for the material to yield slightly in order to maintain a realistic feel while retaining structural integrity for smooth operation. In the FT version, the upper body is covered by a flexible elastic covering 15, and the traveler 25 is coupled to a ring 30 with a surrounding bulging shape simulating the shape of the head of a penis. When the screw shaft 20 is driven in alternate rotational directions, the traveler 25 moves the bulging ring 30 in longitudinally reciprocating motion under the covering 15, simulating the thrusting motion of the head of a penis. The upper body 10 has elongated guide slot(s) (not shown) so that the traveler 25 is constrained to longitudinal movements. Other guide elements to constrain the traveler motion may include guide rods and keyways. The upper body 10 may also assume an appropriate curvature for comfort and positioning.

The covering 15 is constructed from appropriate non-tonic material for tensile strength, flexibility, texture, and durability. The texturing for the cover may include relevant undulations and convolutions of various sizes, shapes, and patterns such as bumps and dimples. The ring 30 is constructed with an appropriate size, shape, and material. The material is selected for to provide the covering 15 with a soft feel and to minimize friction and wear. Ring 30 may be an asymmetric shape other than as shown, and may also include various degrees of texturing. The example of ring 30 shown is not to be construed as limiting in the present invention.

The base portion 35 is constructed from appropriate material such as plastic for strength and rigidity. Since it also functions as a handle for the user as well as a container for the drive components, other ergonomic considerations may apply as layout logistics allow. For example, the shape may be slightly curved for ease of operation without affecting performance and sacrificing component space. The base portion 35 is shown having the motor 40 arranged in line with the circuit board 41, a battery 50 as a power source, and a battery cover 55. A start/stop button 57 is provided on the outside of base portion 35. A motion control switch 60 may also be provided for adjusting the length, speed, and/or frequency of the longitudinal stroke motion. The base portion may have insulating material on its interior walls to insulate the heat of the motor 40 and also to reduce noise for a quieter operation. The base portion 35 can also be used to mount an attached device 98 in proximity to the upper body, such as a vibrator (for clitoral stimulation), miniature camera, or microphone. The camera may also be placed at the tip of the upper body behind a transparent window in the flexible covering so that the liquid-impermeable seal of the upper body is not compromised.

Figure 2A:
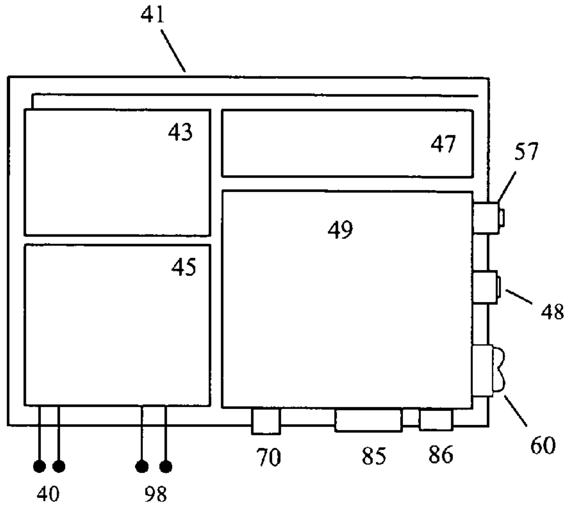
FIG. 2*a* shows an example of a circuit board layout for control of the device.

FIG. 2*a* shows an example of a circuit board 41 for control of the electronic variable stroke device. The circuit board 41 includes a signal transmitter/receiver circuit 43, EPROM 47, IC control circuit 49, and motor controller circuit 45. External leads are provided to the motor 40 and any attached device 98, such as a vibrator, camera, or microphone. The receiving end of the transmitter/receiver circuit 43 can allow downloading of programming instructions and remote control operations, while the transmitting end of the circuit may be used for transmitting feedback signals, such as monitoring the status of the device, i.e. on/off indicator, battery status, malfunctioning circuits, and other useful information.

The Start/Stop button 57 is connected to the IC control circuit 49 and allows the user to manually control the device for extra safety so that the user is able to stop the traveler stroke motion at anytime and to re-start it. The switch 60 is also connected to the IC control circuit 49 and can be used as a selector for motion control, program selection, remote-controlled operation, and/or power-off functions. As a program selector, it can switch between programming routines that are built-in as motion programs (stored in EPROM 47) or those defined by the user. The EPROM may be used to temporarily store user sessions activated by an event-recording button (or switch) 48. This option is available when the user desires to store manually selected stroke and speed movements and is not used with built-in programs. When a program is selected by switch 60, the corresponding instruction set stored in EPROM 47 is fed to the motor controller circuit 45 to carry out the corresponding motor operations. If remote control operation is selected at switch 60, the control circuit 49 passes motor control operations to the transmitter/receiver circuit 43 for remote motor control.

A serial or USB connector 85 and/or communications (wired or wireless) port 86 may optionally be provided for external connection to a computer or other communications device. As noted above, applications programs may be downloaded to the circuit board 41 to be stored on EPROM 47 for user selection and use. It may also be used for transmission of control signals from a remote control unit which the user can operate manually apart from the device. Alternatively, they may be used to either control the device directly from a computer (connected via serial/USB port or communications port 86) using keyboard, mouse, touchpad, or other input devices, or to create or modify user-specific time series signals transmitted to the device. The time series signals may be generated through computer software to produce control signals for controlling real-time position and speed. Programming by software would allow the user to tailor the program to suit individual preferences and save the program files for later use. A power source may also be combined with the communications cable that will enable the device to be operated without batteries allowing the device to be lighter and more maneuverable. A power jack 70 is also provided for recharging the battery or to provide an external power source as an option to battery power.

Figure 2B:
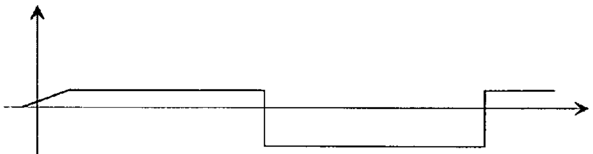
FIGS. 2*b*-2*d* illustrate control signals generated for the longitudinal stroke motion of the device.
Figure 2C:
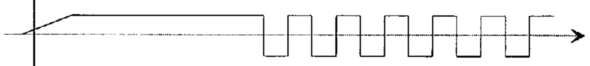
Figure 2D:
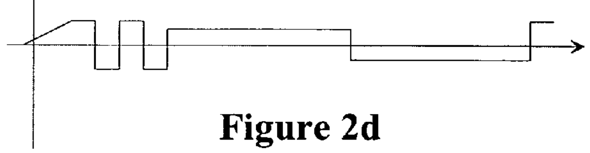

FIGS. 2*b*-2*d* illustrate control signals generated for controlling the motor driving the longitudinal stroke motion of the device. For example, in FIG. 2*b*, the thrust traveler engaged with the rotating screw shaft may be driven to reciprocate along the longitudinal axis at a desired speed, specifically, at a speed which is varied to have a slower movement upward and a faster movement downward (as shown). Another variation is shown in FIG. 2*c*, in which the traveler is driven to move to the top of the stroke and then oscillate with short thrusting movements, or these oscillations may cascade downward. The short thrusting movements may also be provided in the beginning of the stroke and then may proceed to a longer stroke, as shown in FIG. 2*d*. The strokes may be long and slow for massaging effects, or may be short and fast for more concentrated stimulation, or any desired variations in between. There are many other possible variations that may be produced by varying the position and duration of the signals.

Remote Control

As previously described, the FT may also be operated by an optional ergonomic remote control unit for wired or wireless operations. The remote control unit with a wireless connection adds the freedom of wireless control and also multi-user control of the devices in accordance with the present invention. The remote control unit can be held in the user's hand apart from the positioning of the electronic variable stroke device, for ergonomic, intuitive operations.

Figure 3:
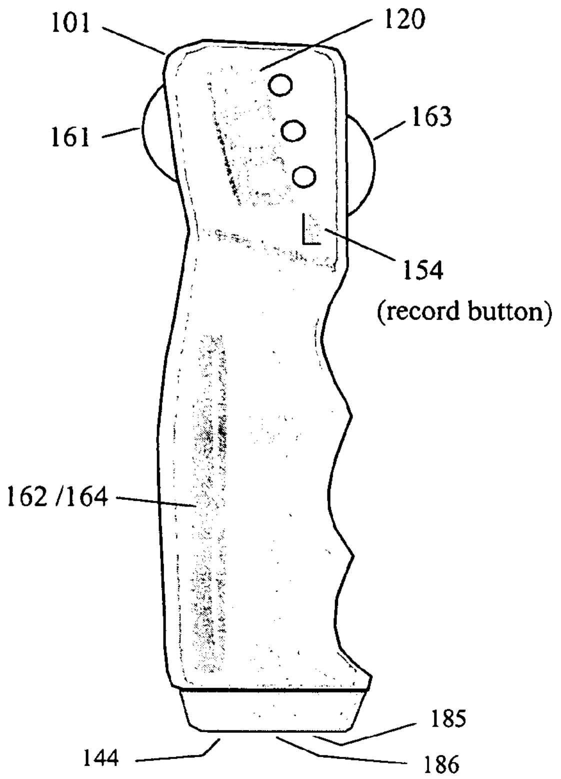
FIG. 3 is an illustration of an ergonomic remote controller unit for remote control of the device.

FIG. 3 shows an illustration of an embodiment of a remote control unit 101 with multi-control and programming means. The remote unit features "thumbwheel" ergonomic controls for stroke position 161 and speed 163 which operate to transmit corresponding control signals to the device through a control and transmitter circuit (not shown). A tactile position indicator 162 (such as a slide knob or row of vibratable elements) may be incorporated in conjunction with a tactile speed indicator 164 such that the user has some indication (or 'feel') of the movements being generated at the receiving end of the device. For example, when the Remote Controller increases the length of the stroke of the device for the user, the user can feel the difference in the stroke length on the handheld unit via the tactile position indicator. In both cases, the slide position or vibrating element can be felt beneath the covering of the handheld unit on the palms of the operator while operating the unit. Although FIG. 3 shows the tactile indicators on one side of the controller, they may also be placed on the other side, opposite sides, or on the back edge of the controller. Other indicators may also be provided in conjunction with this unit such as LEDs for visual information.

The remote control unit may also support pre-programmed functions that may be selected using a program selection switch 120 (shown in FIG. 3 with three selection switches). Instead of using only one EPROM on the device, additional or interchangeable EPROMs may also be used on the remote control unit for expandability and/or as newer programming applications become available. Programs may be entered into the remote control by downloading from an associated computer using port 185 (serial or USB), or communications port 186 (wired or wireless or infrared). A record button 154 for recording sound (by controlling an associated recording device or by controlling a microphone mounted on the device and transmitting the sound signals to an associated computer for playback and/or for programming an event along with the accompanying time series control signals via computer software. The remote control unit may instead have a built-in speaker and microphone for on-board handling of sound. The unit may also support the use of a headset using the headset jack 144. Instead of constructing a new handheld unit, the functions of the remote control unit may alternatively be programmed into a PDA or other wireless handheld device that supports the processing and transmission of device control signals, sound, and feedback indicators and information.

Internet Connection Unit

The electronic variable stroke device of the present invention enables a user to have highly realistic sex or massage stimulation electronically or remotely controlled in an ergonomic fashion so as to maintain a convenient and relaxing environment for sending and/or receiving stimulation. The device is thus readily adaptable to remote control over the Internet or other networks. The possibility of remote stimulation by Internet, for example, opens many opportunities for new and desirable modes of remote, interactive sex or other forms of virtual stimulation for relaxation and pleasure at the user's convenience or in accordance with their individual notions or fantasies, as well as to enhance the physiological or psychological well being of people with physical limitations or disabilities, avoidance of unwanted dating, prevention of transmitted diseases, maintaining marital harmony for couples apart, etc.

Figure 4:
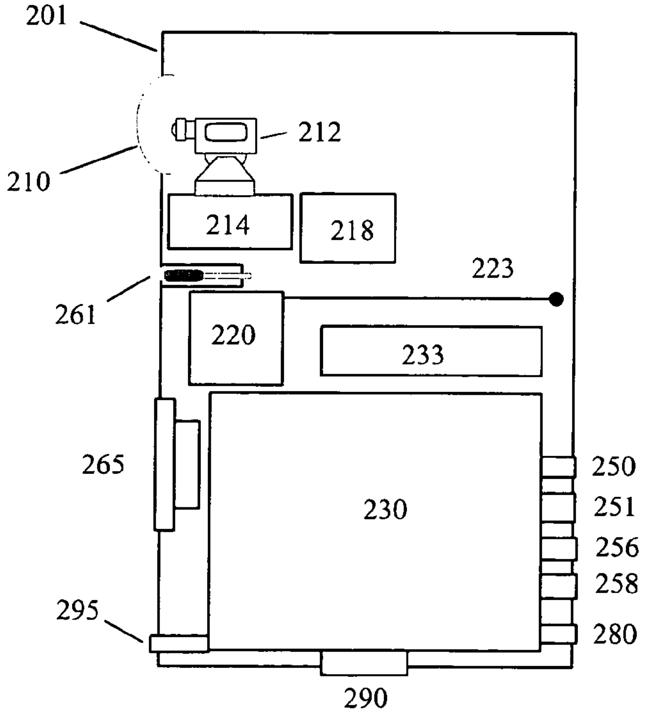
FIG. 4 shows a block diagram of an Internet connection unit for connecting the electronic variable stroke device to the Internet.

As shown in FIG. 4, an Internet connection unit (or "i-conn") 201 is provided as a multi-function platform from which the functions and various uses of one or more associated sex toys may be directed. In a basic mode, the i-conn is provided as an interface between an electronic variable stroke device (e.g., the FT) and an associated computer which has Internet connectivity through a modem or a network interface card (NIC) for Internet access through dialup telephone lines, cable, DSL, LAN, VPN, satellite, Wi-Fi wireless connectivity, etc. The i-conn unit has a device communications port 250 providing a connection for information exchange with the FT, and a computer communications port 251 (such as a serial or USB port or wireless communications port) to the associated computer with the Internet connection. The device communications port 250 may be wireless or infrared corresponding to the port 86 on the FT. The i-conn includes a transmitter/receiver circuit 220, which may include an antenna 223 for wireless transmission, and a main control circuit 230. It may also be used to provide power to the FT or other device via a communications cable. This latter option is implemented in cases where relatively high device power consumption is expected or it is desired to operate the device without the added weight of a battery to make it lighter and more maneuverable.

The i-conn may also provide a means of enabling program selection, switching, and recording user preferences. An onboard EPROM 233 may be used for storing preprogrammed or user defined instructions. Another function of the EPROM is to record the sound or time series signals of FT operations during a session for later use or for incorporation in a user-defined program file. The recorded signals may be transferred later to the computer for file storage and archiving and/or to be retrieved later for future loading and playback. A saved file may be modified on the computer through a software program that enables time series control signals to be edited, altered, combined with sound, etc. The recording of user sessions is initiated by the user using the record button 48 on the FT (see FIG. 1), or the record button 154 on the remote controller 101. A plug-in EPROM may be used for the i-conn EPROM 233 as a means for future expansion, or new programs, or for other applications such as programming vibrator actions, operating expansion mechanisms, and engaging other devices.

Besides using stored or edited programs to control FT motions during a user session, the i-conn permits the FT to be controlled by programs downloaded from a site over the Internet and/or to be controlled directly in real-time by another user who has been granted private access to the first user's session. When an Internet connection is used, programming and control of the device is accomplished through the use of port 251 connected to the computer's corresponding serial or USB port. The Internet access allows programs to be uploaded from and downloaded to the FT's EPROM and may also allow motion signals to be sent to and received from the FT.

The i-conn can also coordinate video camera, audio, and TV display control in conjunction with a user session. For example, the i-conn can include a video camera 212 with a pan and tilt mechanism 214 and zoom control circuit 218, contained within a housing 210 in the i-conn chassis. The i-conn camera may also feature lighting and or light enhancement including night vision. Although FIG. 4 shows the camera mounted towards the top of the i-conn unit, it may also be placed at a separate or external location for better viewing angle and connected to the i-conn. The i-conn may also support a built-in microphone(s) 261 and a speaker system 265. It also has a TV or display output port 256 to output video signals to a television set, display monitor, or projector, and a connector 258 for video camera signal input. The i-conn may also have a connection port 295 for a headset and/or 3-D glasses (or a special i-conn head gear may be supplied with an integrated 3-D display and headset). Power for the i-conn is provided by a built-in ac/dc adapter 280. The i-conn unit may be mounted on a stand or tripod using a mount attachment 290. In this manner, a user during a session can watch their own images and hear their own sounds on the TV display and sound system, or mutually enjoy another user's session to which the first user is connected via Internet, or play back a programmed or recorded session at the user's selection from stored memory.

A biometric card reader may also be installed in the i-conn for monitoring user access to authorized persons, or in a commercial setting may include a payment card reader for membership cards, credit cards, debit cards, smart cards, etc. The i-conn may be provided with full processing capability and an Internet connection method to supplant the need for an associated computer. As a fully functional unit, the i-conn can be sold to individuals at retail or to commercial establishments as a stand-alone model that is plug-compatible with standard types of video cameras and TV monitors. It may also be configured to include functions for standard games for multi-use as a game console as well. Direct Internet access can be enabled using a router and communications card for port 251. With a direct Internet connection, the stand-alone i-conn becomes the main processing center between the FT or other device and a website on the Internet or with another remote user on the Internet who has been granted access to the first user's session (to be discussed below in more detail).

I-Conn Remote Controller

Figure 5:
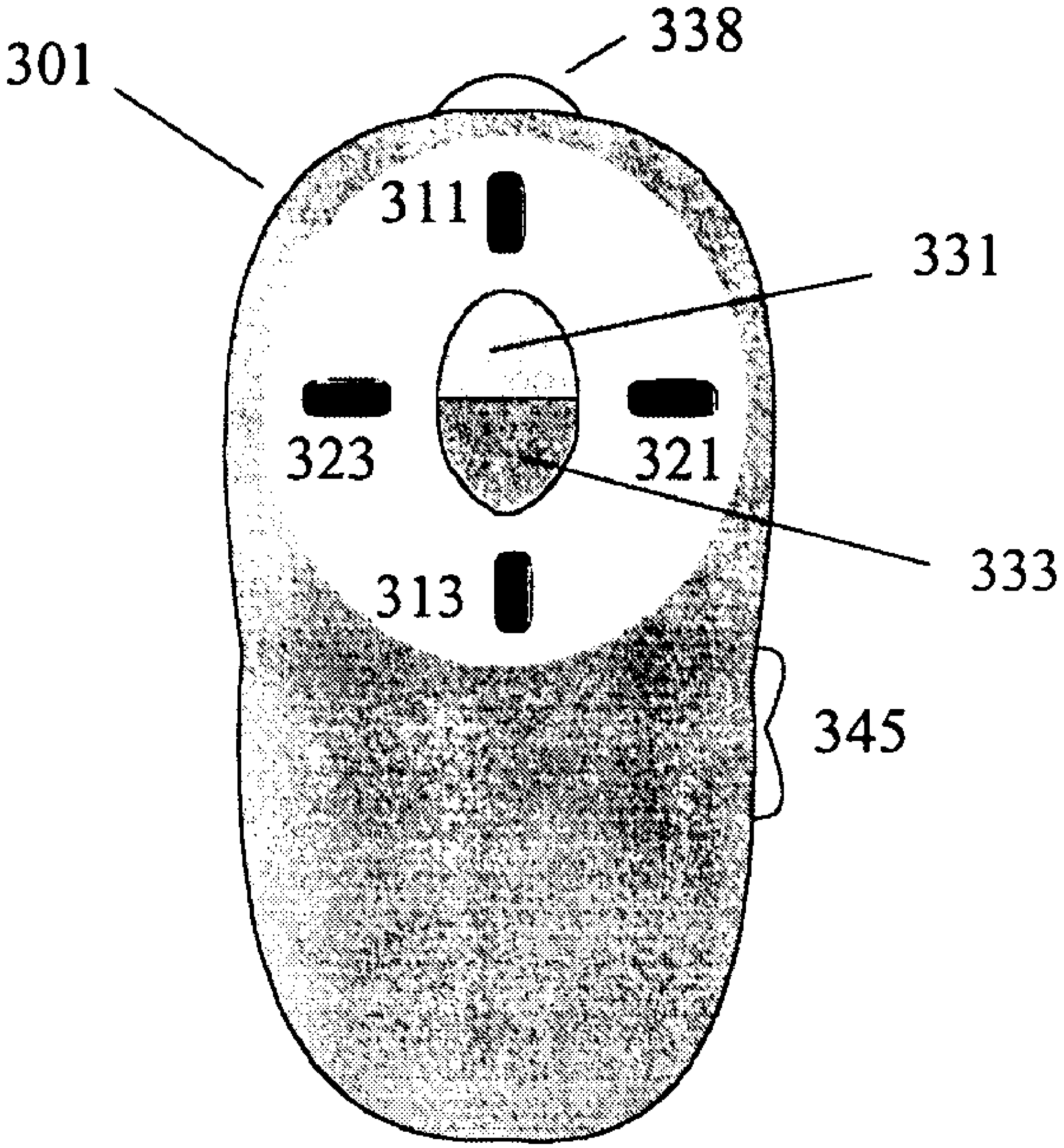
FIG. 5 is an illustration of use of the remote controller unit for the Internet connection unit.

The i-conn unit is intended to be a transparent, plug-and-play type of device which enables remote or virtual control signals to be exchanged via Internet and associated audio, TV display, and video camera components to be interconnected without the user needing to attend to each of the many components. However, for a limited set of basically audio/visual functions, a remote controller 301 as shown in FIG. 5 may be used by the user to conveniently and ergonomically control the i-conn functions. The signals from the controller 301 may be transmitted by wire or wireless operation to the i-conn. The remote controller has camera controls for tilt 311 and 313 (2 directions), pan 321 and 323, and zoom 331 and 333. The camera tilt, pan, and zoom features may also incorporate pre-set functions such that toggling between the settings may be employed during the sessions to enhance the user's experience. The camera zoom may be optical or digital. Special lighting features for dim lighting conditions may be built into the camera, and controlled using the light control switch 338. The remote controller can also have a volume control and a fade control for left and right speakers. When implementing optional microphones (such as on the FT) the sounds may be mixed with a fader control to enhance either signal.

The i-conn may support two (or more) camera ports for multiple camera usage. For added versatility, the i-conn may also provide two (or more) Internet connections as well as control signal channels with switching capability such that the frequencies of the toys/controls may be changed to different channels. For example, 2 people may want to share the experience of interacting together with one or more other partners (a host or hostess). In another example, the user(s) may be able to switch between interacting partners by switching the frequencies.

The remote controller 301 can also control a split-screen or picture-in-picture (PiP) function for the TV display using a split-screen toggle switch 345. This switch becomes active when two camera signals are received. For example, the user of the FT may receive a camera signal from that user's i-conn camera and another signal from a camera of a remote user sent via Internet. Another option that may be implemented by the user is to have two cameras setup in that user's session for viewing different positions of the user, or to receive two camera signals for different viewing positions from a remote user.

Male Toy Device

Figure 6A:
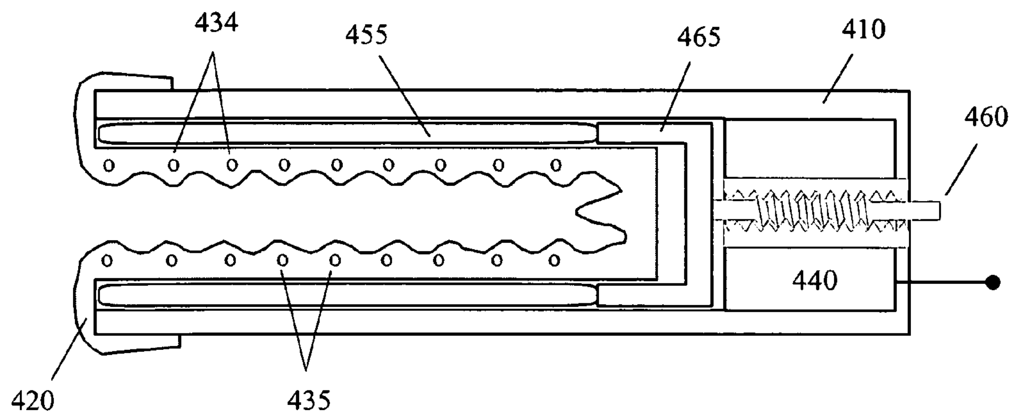
FIG. 6*a* shows a cross-sectional view of the electronic variable stroke device adapted as a male toy device.

As another aspect of the present invention, a male toy device (referred to as "MT") may be provided as a counterpart device to the female toy device so that couples may share a unique form of private interaction. As shown in FIG. 6*a*, the MT includes a housing 410, an inner liner 420, an array of conductive rings including left halves 434 and right halves 435, a main control circuit 440, a fluid cavity 455, a pressure adjusting screw 460, and a pressure cup 465. The housing 410 is constructed from appropriate materials to provide it with structure and flexibility without compromising performance. Design of the housing exterior may include ergonomic considerations whenever possible without affecting performance. The inner liner 420 is constructed from suitable self-lubricating, easily cleanable materials appropriate for its application. There are many materials such as latex, silicon, or other compounds such as "cyber-skin". The inner working surface may also be textured suitable to its application.

The array of rings 430 may be imbedded within the inner liner or may be placed about the outer surface of inner liner. The properties of the rings are such that it is a conductive material and of the correct dimension such as to apply pressure radially inward and retain flexibility under the stresses and strains of use. The rings are formed from two semi-circular or semi-elliptical halves 434 and 435, to form the ring structure. At one end of the ring pair, the proximal ends are quasi-pivotable (due to the flexibility of the material of the inner liner) while the other ends are in electrical contact. One array of semi-circular rings is connected electrically so as to have a common potential while each of the complimentary semi-circular rings has an electrical connection to the control circuit 440. The rings 430 may also be made from a one-piece non-conductive material with a break in the ring. Flexible conductive materials may then be fastened to the rings so that they are in electrical contact at the break in the ring and the contacts are broken as the rings are expanded radially outward. This design may be used to regulate the forces necessary to expand the rings by altering the ring dimensions (i.e., the expansion forces increase with increasing dimensions). For example, the device may be constructed such that the thickness of the rings may decrease as the rings progress inward along the inner liner. Another example may be to have the first ring (or the first few rings) having a thicker dimension. The spacing between the rings may be evenly spaced throughout the longitudinal length, or the spacing may be closer at the beginning and gradually increase towards the end.

In operation, as a male member is inserted in the device, the inner liner 420 is expanded radially outward, and the corresponding ring halves 434 and 435 along the longitudinal axis are forced to break their electrical contact at the contact point of the halves 434 and 435 and in doing so establish a position signal. The control circuit 440 receives the position signal and calculates the time between the previous position signal to output corresponding speed and position signals. These two signals are then transmitted by wire (or wireless) to the i-conn. When these signals are received by the FT, the speed signal is used to set the motor speed and the position signal is used to set the voltage polarity of the motor. Designated ring pairs may also serve to establish synchronization between two toys over an Internet connection. For example, the first and last signals may serve as position markers to coincide with the beginning and ending of a stroke.

A similar method can be achieved for detecting linear transverse motion by using transducers, a linear potentiometer, or an array of magnetic switches. Another method may be the use of infrared sensors to detect longitudinal motion such that beam interruption by the user initiates a signal to be generated.

FIG. 6*a* also shows a mechanism for varying the pressure on the inner liner to increase radial pressure. The housing 410 is threaded at its distal end to accept an adjusting screw 460. The screw rests against a cup 465 at the other end. In operation, as the screw 460 is turned inward into the body, the cup 465 exerts pressure on the fluid cavity thereby increasing the pressure on the inner liner 420. Turning the screw in the opposite direction then releases pressure on the inner liner. This provides a responsive feeling of pressure stimulation around the male member. When the male member is moved back from the device, the ring halves reestablish contact, and the pressure response is released. The MT may be filled with fluid within the cavity 455 formed by the outer surface of the inner liner and the inner surface of the housing. The fluid may be of medical grade silicon, or saline solution, or air that may be held in flexible containers (such as plastic bags). Other substances that are light-weight and somewhat incompressible, such as plastic beads, may also be used.

Figure 6B:
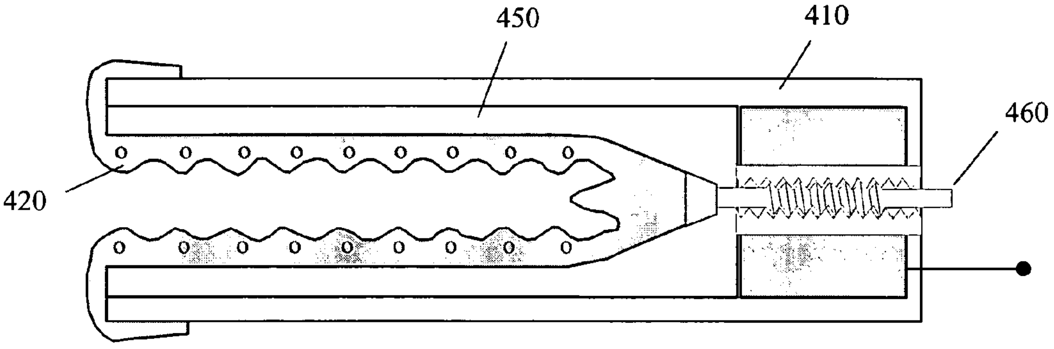
FIG. 6*b* shows a cross-section of a male sex toy device with a variable pressure mechanism.

A more cost effective method for applying radial pressure to the inner liner may be to eliminate the fluid cavity 455 and have an adjustment to the inner liner 420 as shown in FIG. 6*b*. The closed end of the inner liner 420 is attached to the adjusting screw 460 (as in the embodiment previously described) that is threaded into the housing 410. The operation is such that a tension force is applied by the movement of the screw 460 to the inner liner along its longitudinal axis. The amount of radial deflection of the inner liner is controlled by the amount of tension applied to the inner liner. Other means to increase or decrease the pressure on the inner liner may be incorporated. For example, the fluid may be compressed by altering the dimensions of the housing, or with a mechanism to alter the cavity volume.

Pressure sensors may also be placed at the entrance to the inner liner to the MT in order to enhance activity perception to the female user, such as through sound feedback or sending a signal for greater thrusting speed or depth of the thrusting member of the FT. For example, a strain gauge or a burdon tube may be placed at the vestibule of the MT. The signals generated by the MT may be transmitted by wire or wireless to an i-conn unit on the male. partner's side, which sends the signals via Internet to the female partner's FT. The signals are used to correspondingly control the device or mechanism to represent or simulate the corresponding action in the FT. The main control circuit of the MT may also support a camera and or microphone. For example, the camera may be mounted at the end of the inner liner, or on the external surface of the MT. Camera lighting may be controlled via lighting control on the audio/video controller of the male i-conn unit. A microphone on the MT may be placed at the open end of the inner liner or may possibly be mounted together with the external camera.

Interaction by Virtual or Remote Control over the Internet

The above described components of the present invention enable users to have mutual stimulation applied remotely and interactively to each other over the Internet. The following describes certain preferred embodiments for an Internet-enabled interactive system. However, it is to be understood that other types of Internet-enabled systems may be developed given the disclosed principles of the invention.

Figure 7:
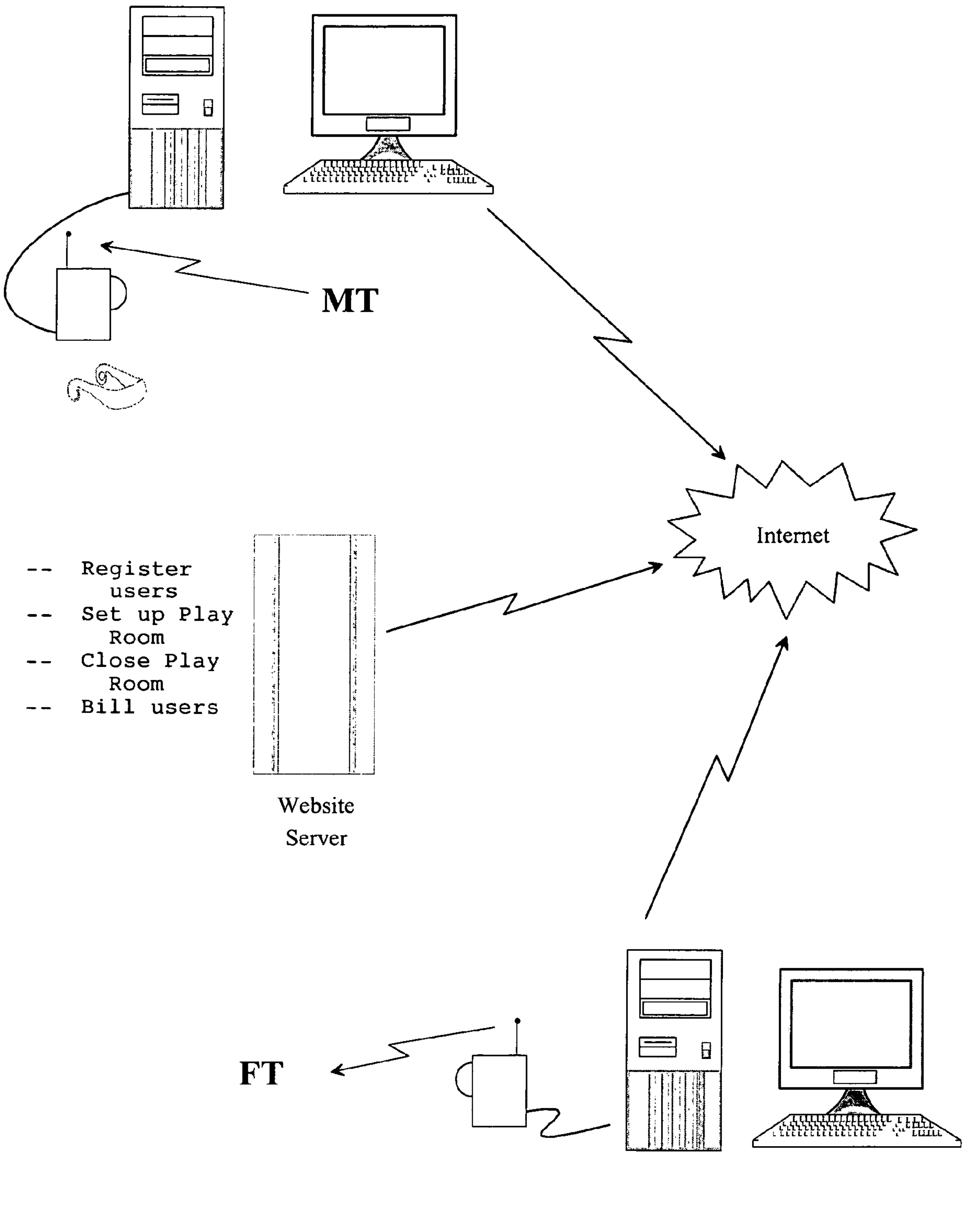
FIG. 7 illustrates an application connecting male and female toy devices for interactive virtual control through an Internet connection.

In a first embodiment, mutual partners will be able to establish their own Internet connection to interact with one another. Couples may prefer this method for long-distance relationships or intermittent job-related separations. Referring to FIG. 7, users will first register on a website (indicated by "Website Server") accessed on the Internet. A user must log in and successfully register a valid identity, payment method, user name and password. After the system confirms the user's name and password, the user may enter the user names of desired partners in the user's personal address book or select from a list of other users interested in meeting partners online. The application program running on the Website Server first validates that the user and selected partner authorize or consent to the virtual interaction (by permission matching or by obtaining actual email consents), then sets up a virtual "Play Room" which the partners will use.

The virtual Play Room serves to establish an encoding method for each partner, initiate a virtual session, then receive, encode, and transmit control signals and associated audio/visual signals from the MT or FT and i-conn of one partner to the other. For example, signals generated by the motions of the MT are directed wirelessly or by wire to the male i-conn. The male i-conn then transfers the signals over the Internet via the Play Room to the female i-conn of the FT user, which will then transmit the received signals to the FT either by wire or wirelessly. The FT then produces the corresponding response in terms of longitudinal position and speed of the thrusting member as dictated by the signals from the MT. In this manner, the partners can enjoy an interactive session of virtual stimulation in the privacy and safety of their own rooms. During the MT/FT interactions, both users can receive audio and video feedback transmitted from the other to their i-conns and connected audio systems and TV displays. Using their remote controller units and i-conn remotes, both users are also in control of their sound and video (camera pan, tilt, and zoom controls) concurrently within the session. The users may use the screen toggle for multiple views, switching views, and other personal viewing preferences. As with the video, the audio signals may be toggled back and forth between the microphone to the user or to sound from the other user at their option. The session may be terminated by either user's indication, or by the expiration of a predefined term for the Play Room. One or both user's accounts may then be billed for the use of the Play Room.

In a second embodiment of an Internet-based interaction system, one or more users will be able to establish group sessions on the Internet for any desired one of a plurality of hosted applications by interaction with a host or hostess and/or other participating users. In the system of the present invention, a unique 3-tiered service structure is established to handle the required functions of the overall system, including, notably, registration, validation of users' identities and payment capabilities, offering a plurality of hosted applications, selecting a hosted application and participants for a group session, managing the group session, closing the group session, and handling billings for the group session. In prior Internet systems, group applications such as chat sites and TGP sites may be single-tiered (direct hosting of application) or may incorporate a double-tiered structure. In a double-tiered structure, an affiliated application may be privately owned and operated under the rules and regulations governed by an upper level host application (or Host site). This individualized open structure leaves the industry reliant upon other businesses for support services such as age verification systems, credit card verification and processing systems, and directories to direct traffic to websites. The structure also enables the common practice of selling IP addresses of users from one company to another. The present 3-tiered structure seeks to obviate these disadvantages while facilitating easy expansion of many and diverse hosted applications and the potential audience of users.

Figure 8:
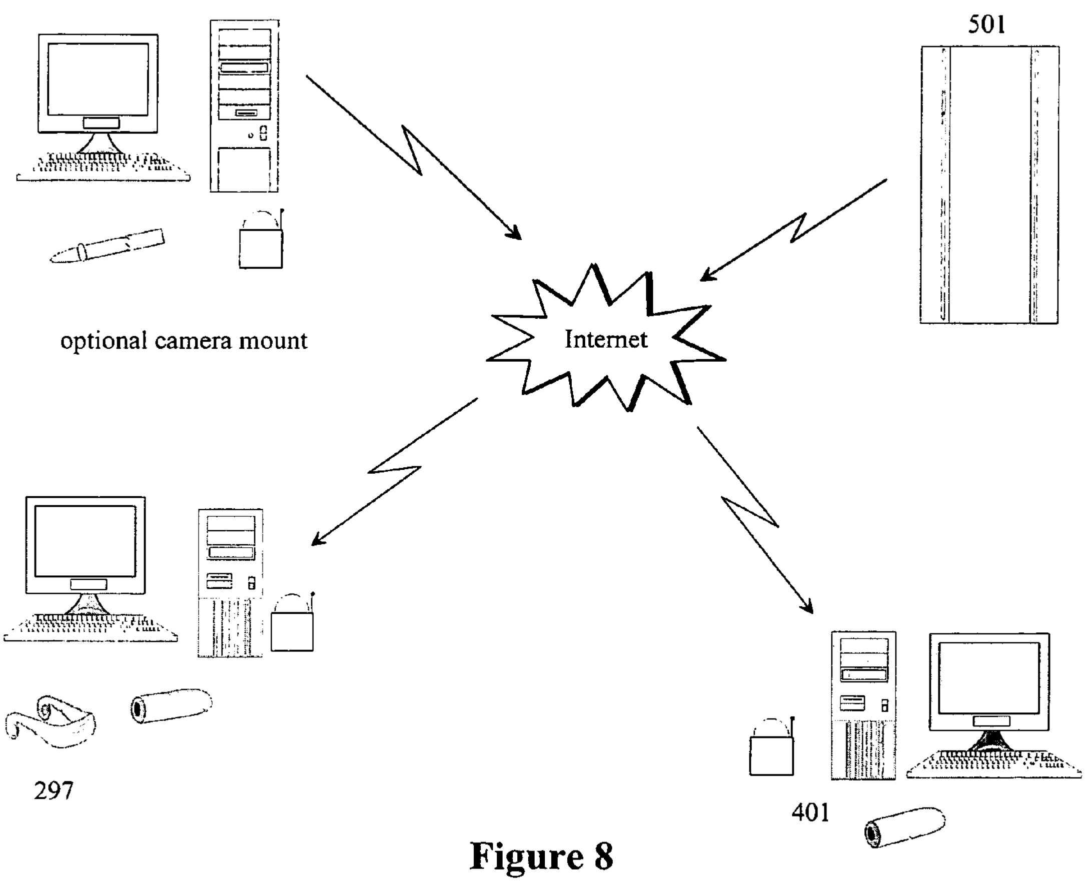
FIG. 8 illustrates a multi-user example of male and female toy devices connected through an Internet connection.
Figure 9:
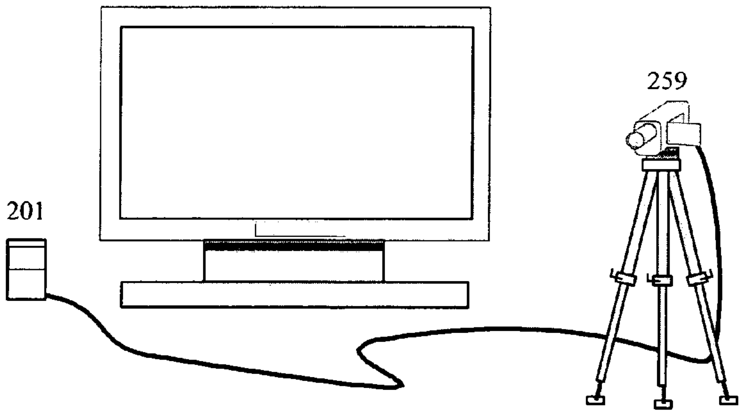
FIG. 9 illustrates optional connection of a video camera and display screen with the interactive virtual control system.

As illustrated in FIG. 8, an Internet host server is used to provide users of FTs and MTs a common access point to make contact with other FT and MT users. The preferred embodiment comprises a system of establishing the business in a 3-tier vertical integration that will be labeled Administrator, Host, and Affiliate Play Host (APH). With a 3-tiered system, the business structure is self-contained and need not rely on outside support business services such as age verification, payment processing, and website directories. Each Host and APH may be individually owned and operated, or there may be many owners, partners, and operators. With the expansion of possibilities for use in various types of group sessions, each user location may be equipped for full video imaging and a compelling screen display for group sessions. This is illustrated in FIG. 9 in which the user's television 257 and camcorder 259 are connected to the user's i-conn 201 at the user's location.

Figure 10:
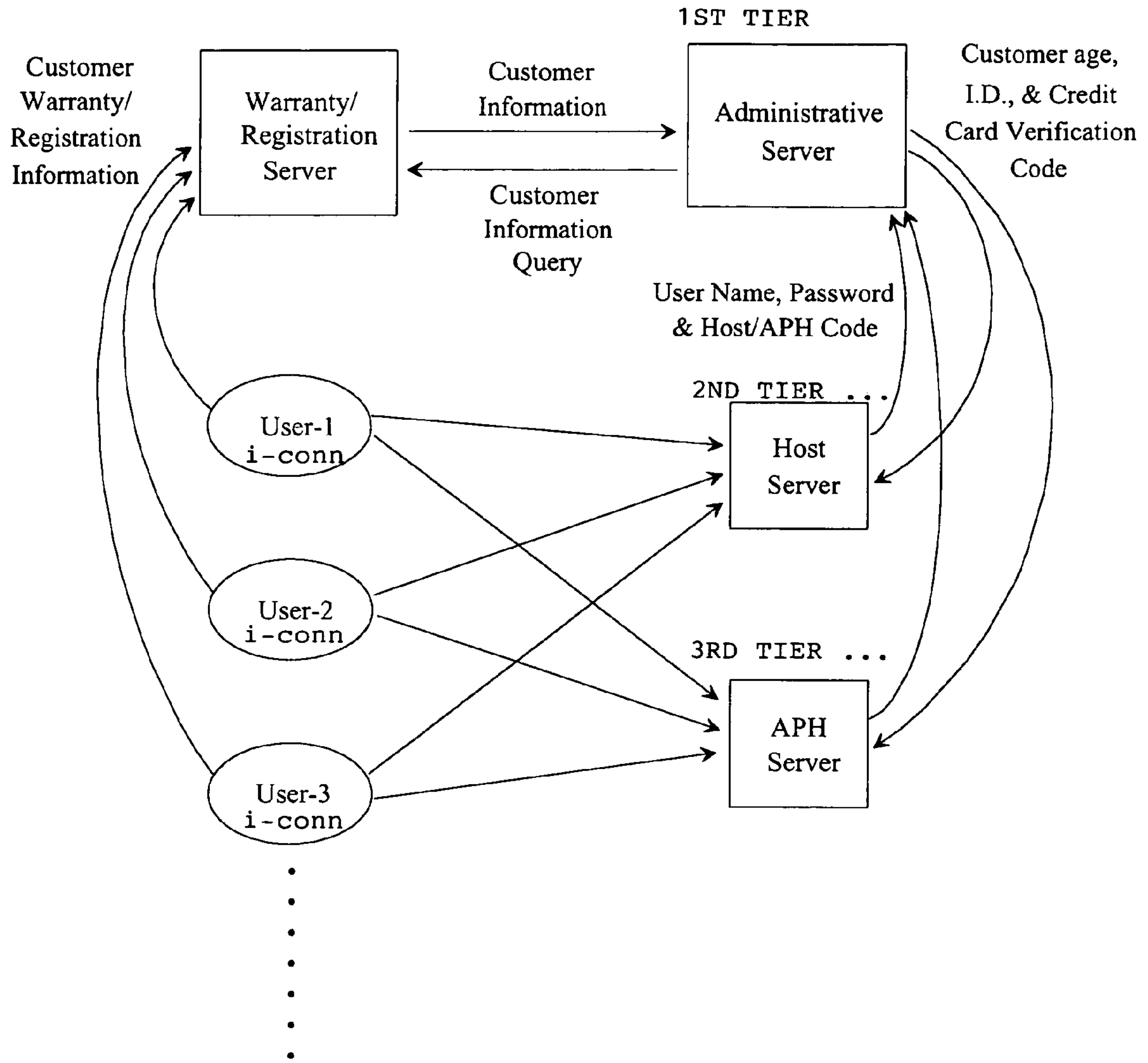
FIG. 10 illustrates a method to implement an Internet-based system for remote interactive play using the electronic variable stroke device.

Referring to FIG. 10, the 3-tier system's Administrator (Administrative Server) is an entity that wholly controls the financial transactions of the customers as well as the financial distribution to its network of Hosts (Host Server) and APHs (APH Server). The Administrative tier provides a solution for the two main problems in the industry. The first is the difficulty in verifying customer identity as a valid cardholder, and the second is the high incidence of credit card chargebacks due to lack of a verification system. The chargebacks may occur due to identity theft or customer fraud. In particular, this system provides anonymity for the customer as the Administrator solely secures and protects the confidential customer data. End user (customer) satisfaction and trust is dependent on a method of transacting payment and personal information securely and discretely and/or anonymously. As the Administrator solely maintains and controls the customer's profile, it is able to collect data that can be utilized for marketing and promotion, research and other benefits. As this customer information is stored in a centralized database, Administrator risk is reduced thereby assuring revenue to the entire system of Hosts, APHs, and other merchants. The Administrator controls, manages, receives, processes, and distributes the funds generated within the system. To accomplish this, the Administrator may establish a bill payment policy with its bank to "pay" multiple accounts. Customer payments can be deposited in the Administrator's checking account to be later distributed to the hosts' and APHs' checking accounts according to the agreed upon revenue split. The Administrator and Hosts will have an agreed upon percentage or rate split and the Hosts will have a similar agreement with their APHs.

One solution to the problem of verifying customer identity and age and payment authenticity is shown in FIG. 10 in which a Warranty/Registration site (server) is used to register all users who have purchased an i-conn for Internet connection of their MT or FT with the Internet group application. An i-conn is required for a user to operate their MT or FT interactively with others. As part of the i-conn purchase transaction, a user will be required to register their i-conn purchase with the Warranty/Registration site. The Warranty/Registration server thus keeps a database of customer records in which each user has made a substantial purchase, has validated a payment method (by which the customers age in excess of juvenile threshold may be establsihed), and has provided some form of identification (including perhaps an i-conn serial or certificate number). If the user desires to register for Internet hosted group applications, the Administrator can validate the registration of the user by confirming the customer information with the Warranty/Registration site.

The second tier of the 3-tier system is the Host tier in which any number of entities can host a type of user community or cluster of user interests. The third tier is the Affiliated Play Host (APH) tier in which any number of other entities may offer a particular interactive service or group service. A Host can host a number of APHs and/or can provide search, review, and commentary services on APHs within its community of interests and links to affiliated APHs. When the customer logs into a Host or APH website, the user name and password, along with the Host and/or APH codes, are transmitted to the Administrator server. The Host and APH may keep records on user names and passwords, however, the user name and customer name may be different for anonymity. The Host and APH codes identify which Host and APH are requested for access by the customer, and also contain information on the agreed upon fees to be divided between Host and APH. After receiving the transmission, the Administrator server queries the Warranty/Registration server for the requested customer information to verify age, identification, and/or payment method. The Administrator site and the Warranty/Registration site may be commonly owned or affiliated so that the exchange of customer information does not violate customer privacy expectations or industry-standard policies. The Administrator server can verify credit card information by subscribing to financial verification systems, such as Credi-Card National Bank or Visa/MasterCard interchange. Upon verification of customer age, identification, and/or credit card approval, the Administrator server then sends a verification (authorization) code to the Host or APH which is then transmitted to the customer in order to enable the i-conn to be enabled for a requested session.

The Administrator may integrate related businesses to increase efficiency (enhance productivity), and promote growth. For example, the business of implementing financial transaction instruments, such as a private label credit card or a smart card with biometrics, can be integrated with a business in toy sales or application services in order to facilitate verification of the person doing the transaction and the account of the cardholder. By encoding the BIOS with the confidential information, it further allows for decreased risk of identity theft. This structure allows Hosts and APHs to operate within a consistent and reliable environment for the sale of toys and related services.

In the preferred embodiment, the Administrator may be vertically integrated under one organization to operate an Internet service for Hosts and APHs providing direct access and quality control of bandwidths, connection speeds, accessibility and availability. This system should provide a competitive advantage and allow for growth opportunities in other areas of interest. The Administrator may also establish a private label credit card or smart card with security measures such as a biometric reader for fingerprint, thumbprint, retina or iris, voice capture, etc., as a means to more accurately verify the customer against the stored biometric file in the Administrator database. A smart card may be read by the i-conn's built-in biometric reader, and that identification can be matched to the biometric file that may be secured with the warranty card information. The biometric cards should increase the accuracy rate of identifying cardholders as well as eliminating the need for cardholder to remember a PIN number. The procedure of scanning the biometric for the stored biometric file may be setup at the card issuer's location. The biometric files may also be used in conjunction with customer warranty or registration information for added security. This feature also enables the i-conn to be a standalone model as previously discussed. The smart card holds the cardholder's personal data and account reference information. The EEPROM (Electrically Erasable Programmable Read-Only Memory) storage on the card of an electronic purse in which money is able to be repeatedly loaded and spent onto the smart card for the duration of the card. Smart cards can be issued in various forms: use as a debit card (works as a check in which customer's account is debited for sale. The debit can take place immediately at time of sale); e-cash or e-purse (works as a prepaid card) or a credit card. Smart cards may be restored with new amounts of funds after reaching a zero balance. In addition, the private label and smart cardholders of the system may also be eligible to utilize the ISP Service.

The primary function of the Host is to promote its user communities and market the APHs. Hosts provide management, operational, technical, and other business support. Another function is to broadcast (unicast or multicast) live audio/video streams to spectator(s) generating additional revenue. Hosts can encrypt the streams to prevent copying. The Host may also record the audio/video interaction which may be purchased by the spectator(s). The purchased recorded event may then be downloaded into a file to the spectator or may be available on disk format. The host website requires customer verification to gain entry into the website which may include a user or login name, and password. For the purpose of anonymity, the customer may enter a user (login) name of choice. The host website may provide photos to enable customers to easily view and select an APH and may also display information on the availability of the APH, for example, Available and Online, Busy and Online, or Offline.

The primary function of the Affiliate PlayHosts (APH) is to provide quality entertainment services and customer interactions at the PlaySite. The PlaySite may be an actual physical location where an APH server is located to manage interactions of online customers with local customers attending at the physical location. The APHs are a very critical part of the system structure as they provide the human interaction with the end user or customer. The APH may consist of one or more entities providing interactive services using the FT and MT toys and controls to one or more online customers. As part of their services, an APH should provide the proper atmosphere to all of their customers, both online and present locally. Props and costumes may be offered locally or presented online according to the theme of the APH. For example, an APH PlaySite may be decorated as a theme environment with props such as a bed, bathtub, shower, etc. The PlaySite may have one or more PlayRooms, each of which may be hosting a different group session. With wireless connectivity, the APH server may also be located outdoors to provide the proper atmosphere as desired such as at a poolside, or in a secluded backyard, or beach, forest, etc. Some background scenery may also be projected onto a screen (walls, ceiling, etc.) to provide the proper ambiance.

Online customers may connect to the APH server directly or via the Host website. Customers may also select a time and date to interact with an APH PlaySite. A login and password is required to enter the online PlaySite. After the online customer selects an APH, a live real-time encrypted audio/video stream is exchanged, and the online customer and APH can interact directly on a personal level utilizing the FT or MT toy or control. Affiliates may offer services for FT users, MT users, or both to accommodate single or multiple users. There may be many combinations of single users such as, FT to MT, FT to FT, etc. An APH may provide services to accommodate 2 (or more) users as shown in FIG. 8. For this type of application, the i-conn may be enhanced to add more transmitter/receiver circuits and frequencies. The i-conn may have a selection switch to select the number of channels or in the case of wired devices, the selection is made by simply plugging into connectors. The number of devices that the i-conn can manage may be limited by cost, bandwidth, and limitations to the number of floating frames that can be placed on the display. The FT (or MT) devices may need to differentiate these frequencies. The FT (or MT) devices may be sold with certain frequencies, or the frequencies may be selected on the device. A professional model of the i-conn may be developed for APHs with the addition of more channels to the i-conn circuit with a means to switch channels, and to accommodate multiple users for both FT and MT.

The participant users have the option of switching between cameras and with multiple frames on their display. Cameras may be provided by the APH at the physical PlaySite and may be positioned according to the operator's preference. The users may then be able to control the pan, tilt, and zoom on their respective cameras to view the APH and the PlaySite.

For suitable public events, an APH may also broadcast the interactions to nonparticipating spectators who just want to observe the interactions with feedback through an MT or FT. Non-participating spectators may log-in to a spectators' gallery provided by a Host website. A short preview of a real-time interactive session may be provided before the spectators commit to viewing the offered sessions. Mutual authorization must be received from a customer if the customer screen is part of the broadcast. The session may be streamed live on a secured and encrypted connection to the Host for broadcasting. The spectators will be unable to copy or save the broadcasting due to the encryption. Spectators will be able to download special software for viewing purposes. The spectators may also be offered control over cameras provided by the APH (similar to the participant user). The spectators may then be able to control the pan, tilt, and zoom on their respective browsers to view the APH and the PlaySite. The spectators may be allowed access to all or some of the camera video images at the discretion of the APH. The spectators may also use camera switching to view different angles and digital zoom control to zoom on the video images. The control for the camera may be by keyboard, mouse, or other control unit to be purchased.

For a typical transaction, the customer must provide their registered password to gain entry into a Host website and may browse through some sample selections before selecting an APH. This password may be used in lieu of age verification as this has been previously verified by the Administrator via access to the warranty information of the registered i-conn. When the customer selects an APH, the connection is transferred to that APH along with the user name and password. The customer may then browse through the APH PlaySite and interact with lounge hosts or other customers. The customer may request a transaction that requires a credit card (or payment) verification process. During the verification process, the customer is temporarily routed on a secured connection to the Administrator server to fill in the credit card or other payment information. The Administrative server may verify the customer information by comparing customer information previously stored on the database of the Warranty/Registration site or may use a financial verification service. The Administrator then sends an authorization code back to the APH and the service connection can be activated. The customer is then transferred back to the APH connection.

When the customer and APH begin a session (via secured and encrypted connection), either the Administrator or Host server begins polling the connection. The polling is used to determine the interaction time in order to calculate per minute rates. An alternate method to polling may be to have a termination signal generated by the APH server to mark the end of the transaction (EOT), and this signal is then forwarded to the Administrator server. At the conclusion of the session or the termination of the connection (which may be terminated at any time by either the customer or APH), the polling server or EOT signals the end of the connection. After receiving a termination signal, the Administrator Server may then compute the billing of the customer and may then transfer the allocated funds to the accounts of the respective Hosts, APH, and Administrator. The customer may also verify the service time and charges.

In one typical application example, the customer may be using the i-conn with the optional TV and webcam port, and the AP host may have its i-conn connected to one or more webcams with a CRT or LCD display at the PlaySite. At the APH physical PlaySite, the AP host/hostess may have a suitable environment with lighting controls with the cameras strategically placed. The interactive session may begin with light conversation perhaps setting the mood, adjusting the camera angle, setting the volume control, and lighting. The attention of the participants may then begin to focus on operating the FT or MT according to mutual comfort levels. During this time, the user may be operating the camera controls such as pan, tilt, and zoom, as well as switching to the different APH cameras. Since the participants connected through the PlaySite can see and hear each other, visual as well as audio commands may be exchanged. With each verbal command or visual signal, the appropriate control for the toy may be initiated. If contraction/expansion devices are incorporated into the toy, then other control words or actions may be used.

As additional model for revenue-generation, the interaction may also be recorded by the Host or APH and made available for pay-per-view by other customers or non-participating spectators. In some cases, the customer(s) or spectator(s) may want a recording as a memorabilia, or gift. The purchased recorded event may then be downloaded into a file to the customer or may be available on disk format. An advantage to a CD is that the performers may be able to autograph or personalize the CD or packaging to create extra value. Customers may strive for a collection of CDs from different performers. Personal items of memorabilia of the performers may also be available for customer purchase. For spectator recordings, control signals may not be included with the a/v signals however, for customer recordings, the control signals may be included with the a/v signals.

While the above-described example is a one-to-one application where one customer is interacting with one AP Host/Hostess, it is equally applicable to a group application where any number of customers (users), AP hosts/hostesses, FT, MT, FT controls, and MT controls may be signed on. As is typical of the adult entertainment industry, there may be thousands of sites covering every conceivable theme, fantasy, or subject area. Customers can choose any type of playroom to reflect a desired theme, scene, location, or scenery. For example, playsites may be created around scenes from a movie or novel, period in history, futuristic scene, etc. Costumes, hairstyles, and jewelry may be provided to reflect different cultures and historical scenes. The customer may also choose the type of hosts/hostesses by their performances, by user preference, or by their spoken language or accents. Other props to support the theme or ambiance may also be included such as furniture, lighting, extra cameras, or other special effects.

Other Types of Group Sessions

The above-described system of conducting virtual interactive group sessions using an interaction device at the remote user's location can also be applied to videoconferencing. Conventional videoconferencing only displays split-screen images and sounds; for 3 or more people in real-life conference rooms in separate locations, the system becomes inefficient. In the present system, a "virtual conference room" can be established by an APH in which the video images of the participants are pasted in respective positions or on respective avatars positioned in the virtual conference room. The remote i-conn can strip the image of each person from their background and only the image of the person will be used for transmission. This will reduce bandwidth to improve the performance of the interactive conferencing. The need for split-screen displays of 3 or more images will be eliminated and replaced by the virtual conference room.

Another embodiment is to provide a "virtual playroom" (similar to virtual videoconferencing) in which an AP host/hostess will have their interaction viewed within a virtual playroom. This system will make it possible to have even an APH Host invited to be present with other APHs in the virtual playroom. This feature may be accomplished through visual effects such as chroma keying (aka "blue/green screen compositing" as used in the movie/television industry). The invited "guest" APH person(s) can interact in front of a blue screen. The web camera images of the guest APH person(s) may then be streamed to the APH site that is hosting the virtual playroom interaction. The images of the guest AP person(s) may then be combined with other guest AP person(s) along with the host AP person(s). The combined images may then be streamed to customers and spectators. This expands the possibilities for virtual group interactions with different APH person(s) who can provide enhanced thematic, fantasy, or scenic content.

Another variation is to have customers interact with animated characters in a virtual playroom. Using motion capture and rendering technology, an APH can convert AP host actions (motion capture) and superimpose an animated character image onto the movements (rendering) which the customer then views as a seamless animated character. Customers may also have access to motion capture and rendering technology to create their own animated characters, which also provides them with anonymity for broadcasting to public spectators. This system may also offer some APHs to specialize in interactions with celebrities such as film and television personalities, musicians, politicians, and athletes.

Other Toy Embodiments

Figure 11:
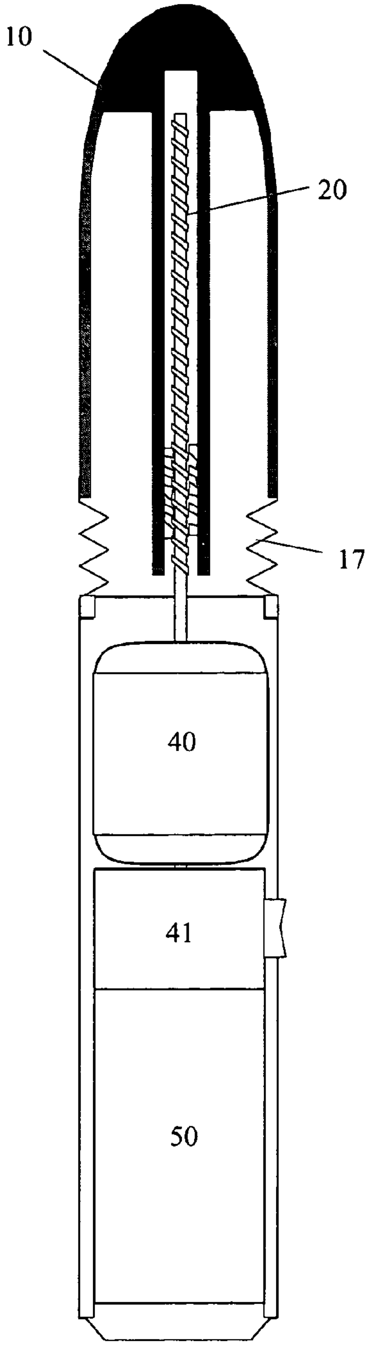
FIGS. 11 and 12 show cross-sectional views of other embodiments for the electronic variable stroke device.

FIG. 11 shows another preferred embodiment of the female toy device. In this embodiment, the traveler and upper body have been combined to form an integral member 10 which is engaged with the threading of the screw shaft 20 for longitudinal reciprocation movements relative to the base portion. A covering 17 is shown with elastic folds to compensate for the reciprocation movements. It can also be made from a flexible or stretchable material to expand and contract without binding; and therefore, eliminate the folds in the covering.

Figure 12:
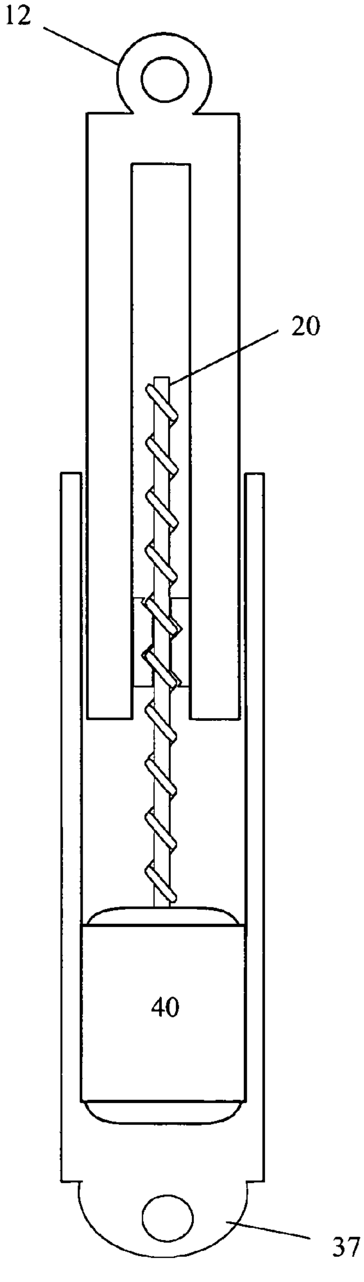

FIG. 12 shows another embodiment adapted for powering reciprocation movements in other types of toys or game devices. In this case the traveler and the upper body have been combined to form oscillating traveler member 12 engaged with the screw shaft 20 which slides in telescoping fashion in the base portion 37. The traveler member 12 and base portion 37 have rings or joints on their distal ends for connecting between the toy parts to be engaged in reciprocation movement. A control circuit may provide a simple timed control signal applying voltage directly to the motor 40. This embodiment may be useful to replace the "hydraulics" commonly used in toys or other devices with a more precise, variably controllable device. The movement of the traveler can be registered as signals to the circuit for use in feedback and ergonomic control systems. Relative movement between the upper and lower bodies will result in a voltage at the motor terminals that can be interpreted by the circuit and applied for corrective or adjustment movements by discrete voltages applied to the motor. In a similar fashion, the device can be used as servo mechanism using the motor, screw, traveler and control circuit for precise control of continuous degrees of variable motion.

In summary, the electronic variable stroke device enables a user to enjoy stimulation by remote or virtual control to address physiological and psychological needs of individuals for total well being. This device overcomes the restrictions of the reciprocating motion of other current devices having equivalent objectives. The user has the flexibility to operate the device from the ergonomic remote, for easier and intuitive use of the controls or for added operational variability. The remote control unit is also capable of connecting to the Internet or other wireless communication devices to program the device for broader operations and future options, and to receive relayed operating signals from a corresponding device to provide the appropriate actions or responses. The system enhances the sense of touch stimulation through audio, video, and mechanized feedback and response. Interaction via touch and related feedback control can raise the level of communication between individuals to an intimate and personalized form. Long-distance personal yet safe and disease-free contact with loved ones, new partners, and fantasy partners can be achieved.

It is to be understood that many modifications and variations may be devised given the above description of the principles of the invention. It is intended that all such modifications and variations be considered as within the spirit and scope of this invention, as defined in the following claims.

The invention claimed is:

1. An electronic variable stroke device comprising:

a base portion containing a motor and power source for rotating a screw shaft alternately in opposite rotational directions, an upper portion extending longitudinally from the base portion and having a flexible cover layer connected to a proximal end of said base portion and extending around a tip end of the upper portion, wherein the rotary-driven screw shaft has a length extending longitudinally into the upper portion to said tip end thereof and is provided with screw threading thereon, and a screw-thread traveler or follower having a bulging contour projecting against the flexible cover layer so as to create a bulging contour on an external side of the cover layer, said screw-threaded follower being positioned within the upper portion and engaged with the screw shaft threading in order to drive the bulging contour formed on the external side of the cover layer in reciprocating longitudinal motion;

and further comprising electronic controls provided in said base portion for controlling rotation of the screw shaft to vary the length, speed, and frequency of the bulging contour on the external side of the cover layer in variable-stroke reciprocating longitudinal motions.

2. An electronic variable stroke device comprising:

a base portion containing a motor and power source for rotating a screw shaft alternately in opposite rotational directions, an upper portion extending longitudinally from the base portion, wherein the rotary-driven screw shaft has a length extending longitudinally into the upper portion and is provided with screw threading thereon, a screw-thread traveler or follower positioned within the upper portion and engaged with the screw shaft threading in order to drive a member constituting a part of the upper body in reciprocating longitudinal motion, and electronic controls provided in said base portion for controlling rotation of the screw shaft to vary one or more of the length, extent speed, and frequency of the upper body member's reciprocating longitudinal motion, wherein said electronic controls include a memory for storing motion programs therein for operating the device in different programmed modes of reciprocating longitudinal motions.

3. An electronic variable stroke device according to claim 2, wherein said electronic controls include a transmitter/receiver for sending and receiving control signals for operating the device to and from an external source.

4. An electronic variable stroke device comprising:

a base portion containing a motor and power source for rotating a screw shaft alternately in opposite rotational directions, an upper portion extending longitudinally from the base portion, wherein the rotary-driven screw shaft has a length extending longitudinally into the upper portion and is provided with screw threading thereon, a screw-thread traveler or follower positioned within the upper portion and engaged with the screw shaft threading in order to drive a member constituting a part of the upper body in reciprocating longitudinal motion, and electronic controls provided in said base portion for controlling rotation of the screw shaft to vary one or more of the length, extent, speed, and frequency of the upper body member's reciprocating longitudinal motion, and including a transmitter/receiver for sending and receiving control signals for operating the device to and from an external source, wherein said electronic controls include a memory for storing motion programs for programmed operation of the device sent from an external source.

5. An electronic variable stroke device according to claim 3, wherein said electronic controls include a memory for storing motion programs derived from the user's manual operation of the device, said transmitter/receiver being used to send a stored motion program from the user's manual operation of the device to an external source.

6. An electronic variable stroke device comprising:

a base portion containing a motor and power source for rotating a screw shaft alternately in opposite rotational directions, an upper portion extending longitudinally from the base portion, wherein the rotary-driven screw shaft has a length extending longitudinally into the upper portion and is provided with screw threading thereon, and a screw-thread traveler or follower positioned within the upper portion and engaged with the screw shaft threading in order to drive a member constituting a part of the upper body in reciprocating longitudinal motion, which is adapted as a female toy, wherein said upper body is formed with an outer covering and a bulging annulus member coupled to said traveler which is driven in longitudinal reciprocation under said outer covering to simulate the thrusting motion of a penis.

7. An electronic variable stroke device comprising:

a base portion containing a motor and power source for rotating a screw shaft alternately in opposite rotational directions, an upper portion extending longitudinally from the base portion, wherein the rotary-driven screw shaft has a length extending longitudinally into the upper portion and is provided with screw threading thereon, and a screw-thread traveler or follower positioned within the upper portion and engaged with the screw shaft threading in order to drive a member constituting a part of the upper body in reciprocating longitudinal motion, which is adapted as a female toy, wherein said upper body has a rounded outer shape and is formed integrally with said traveler and driven in longitudinal reciprocation to simulate the thrusting motion of a penis.

8. An electronic variable stroke device comprising:

a base portion containing a motor and power source for rotating a screw shaft alternately in opposite rotational directions, an upper portion extending longitudinally from the base portion, wherein the rotary-driven screw shaft has a length extending longitudinally into the upper portion and is provided with screw threading thereon, and a screw-thread traveler or follower positioned within the upper portion and engaged with the screw shaft threading in order to drive a member constituting a part of the upper body in reciprocating longitudinal motion, which is adapted as a device for driving a part of a toy, wherein said upper portion is coupled to said traveler and has a first joint member on a distal end thereof, said base portion has a second joint member on a distal end thereof, and said first and second joint members are used to couple the device between a stationary part and a driven part of a toy.

9. An electronic variable stroke device comprising:

a base portion containing a motor and power source for rotating a screw shaft alternately in opposite rotational directions, an upper portion extending longitudinally from the base portion, wherein the rotary-driven screw shaft has a length extending longitudinally into the upper portion and is provided with screw threading thereon, and a screw-thread traveler or follower positioned within the upper portion and engaged with the screw shaft threading in order to drive a member constituting a part of the upper body in reciprocating longitudinal motion, and further comprising a hand-held remote controller unit which is used by the user for ergonomic control of the operation of the device.

10. An electronic variable stroke device according to claim 9, wherein said remote controller unit includes electronic controls provided therein for controlling rotation of the screw shaft to vary one or more of the length, extent, speed, and frequency of the upper body member's reciprocating longitudinal motion.

11. An electronic variable stroke device according to claim 10, wherein said electronic controls include a memory for storing motion programs therein for programmed operation of the device.

12. An electronic variable stroke device according to claim 10, wherein said electronic controls include a transmitter/receiver for sending and receiving control signals for operating the device to and from an external source.

13. An electronic variable stroke device comprising:

a base portion containing a motor and power source for rotating a screw shaft alternately in opposite rotational directions, an upper portion extending longitudinally from the base portion, wherein the rotary-driven screw shaft has a length extending longitudinally into the upper portion and is provided with screw threading thereon, and a screw-thread traveler or follower positioned within the upper portion and engaged with the screw shaft threading in order to drive a member constituting a part of the upper body in reciprocating longitudinal motion, and further comprising a network connection unit for accessing a network and for sending and receiving control signals for operating the device to and from an external source on the network.

14. An electronic variable stroke device according to claim 13, wherein said network connection unit includes electronic controls for controlling audio/visual components connected to said unit, and for sending and receiving audio/visual signals in conjunction with operation of the device to and from an external source on the network.

15. A system for conducting an interactive session of a user with an external service accessible on a network comprising:

an electronic variable stroke device comprising a base portion containing a motor and power source for rotating a screw shall alternately in opposite rotational directions, an upper portion extending longitudinally from the base portion, wherein the rotary-driven screw shaft has a length extending longitudinally into the upper portion and is provided with screw threading thereon, a screw-thread traveler or follower engaged with the screw shaft threading in order to drive a member constituting a part of the upper body in reciprocating longitudinal motion, and electronic controls include a transmitter/receiver for sending and receiving control signals for operating the device;

a network connection unit for accessing a network and sending and receiving control signals for operating the device to and from an external service on the network; and an external service accessible on the network having means for sending and receiving control signals for operating the device.

16. A system for conducting an interactive session of a user according to claim 15, wherein said network connection unit includes electronic controls for controlling audio/visual components connected to said unit, and for sending and receiving audio/visual signals in conjunction with operation of the device to and from said external service on the network.

17. A system for conducting an interactive session of a user according to claim 15, wherein said external service conducts an interactive session with a user by transmitting control signals generated by said external service to the user's network connection unit for operation of the user's device.

18. A system for conducting an interactive session of a user according to claim 15, wherein said external service conducts an interactive session with a user by receiving control signals generated by another user and transmitting them to the user's network connection unit for operation of the device.

19. A system for conducting an interactive session of a user according to claim 18, wherein said other user is provided with an electronic stimulation device having electronic controls include a transmitter/receiver for sending and receiving control signals for operating the device, and a network connection unit for accessing the external service on the network similar to the first-mentioned user.

20. A system for conducting an interactive session of a user according to claim 19, wherein said first-mentioned user and said other user exchange control signals through said external service on the network to each other's network connection unit to control the operation of each other's electronic stimulation device for mutual interactive stimulation.

21. A system for conducting an interactive session of a user according to claim 19, wherein said electronic variable stroke device of the first-mentioned user is a female toy and said electronic stimulation device of the other user is a male toy.

22. A system for conducting an interactive session of a user according to claim 19, wherein said network connection units of said first-mentioned user and said other user each includes electronic controls for controlling audio/visual components connected to said unit, and for sending and receiving audio/visual signals to each other's network connection unit in conjunction with the operation of each other's electronic stimulation device.

23. A system for conducting an interactive session according to claim 15, further comprising:

each user having an electronic stimulation device provided with electronic controls include a transmitter/receiver for sending and receiving control signals for operating the device, and a network connection unit for accessing the external service on the network and for sending and receiving control signals for operating the device to and from the external service, said network connection unit having electronic controls for controlling audio/visual components connected to said unit, and for sending and receiving audio/visual signals to and from the external service on the network in conjunction with operation of the device;

an external service accessible by said network connection unit on the network, said external service having means for establishing an interactive session with the plurality of users and for sending and receiving control signals and audio/visual signals via each user's network connection unit for operating each user's device and audio/visual components, wherein said external service on the network has a 3-tiered service structure of:

an administrator tier for registering the identities of authorized users of the external service and for managing billing and payment methods of the users;

a host tier for promoting a community of users and marketing hosted interactive session services to said community of users; and an affiliated playhost tier for providing interactive session services of other external playhost services on the network to users referred or linked from said external service.

24. A system for conducting an interactive session according to claim 23, wherein an interactive session service is conducted for a plurality of users as a videoconferencing session in a "virtual conference room", and video images of the users are pasted in respective positions or on respective avatars positioned within the virtual conference room.

25. A system for conducting an interactive session according to claim 15, further comprising:

each user having the electronic variable stroke device and the network connection unit for accessing the Internet and for sending and receiving control signals for operating the electronic input/feedback device to and from an external service on the Internet, said network connection unit having electronic controls for controlling audio/visual components including an video camera and a display screen connected to said unit and for sending and receiving audio/visual signals to and from the external service on the Internet in conjunction with operation of the device;

an Internet website accessible as an external service on the Internet through said network connection unit of each user;

said Internet website having means for establishing an interactive session with the plurality of users and for sending and receiving control signals for operating the electronic variable stroke device and the audio/visual components of each user;

wherein said Internet website has a 3-tiered website structure of:

an administrator tier for registering the identities of authorized users of the external service and for managing billing and payment methods of the users;

a host tier for promoting a community of users and marketing hosted interactive session services to said community of users; and an affiliated playhost tier for providing interactive session services of other playhost websites to users referred or linked from said Internet website.

26. A system for conducting an interactive session according to claim 25, wherein said 3-tiered website structure further includes a warranty/registration site accessible by at least said administrator site to which a user who has purchased an Internet connection unit is required to transmit the user's identity and payment method information, said warranty/registration site being enabled to respond to inquiries from said administrator site to verify the identities and payment methods of users requesting access to an interactive session service.

27. A system for conducting an interactive session according to claim 25, wherein an interactive session for a plurality of users is conducted by an affiliated playhost site offering a specific interaction session service requested by the users.

28. A system for conducting an interactive session according to claim 27, wherein the interactive session service conducted by said affiliated playhost site includes providing audio/visual content from a physical location hosted by the affiliated playhost in conjunction with the specific interaction session service.

29. A system for conducting an interactive session according to claim 27, wherein the interactive session service conducted by said affiliated playhost site is made accessible online for viewing by other non-participating spectators.

* * * * *